(12) United States Patent
Rouge

(10) Patent No.: US 10,208,072 B2
(45) Date of Patent: Feb. 19, 2019

(54) UNIVERSAL ENZYME RESPONSIVE LINKER FOR ASSEMBLING LIGANDS ON DNA FUNCTIONALIZED NANOMATERIALS

(71) Applicant: University of Connecticut, Farmington, CT (US)

(72) Inventor: Jessica Lynn Rouge, Glastonbury, CT (US)

(73) Assignee: University of Conneticut, Farmington, CT (US)

( * ) Notice: Subject to any disclaimer, the term of this patent is extended or adjusted under 35 U.S.C. 154(b) by 0 days.

(21) Appl. No.: 15/917,911

(22) Filed: Mar. 12, 2018

(65) Prior Publication Data

US 2018/0258114 A1     Sep. 13, 2018

Related U.S. Application Data

(60) Provisional application No. 62/470,327, filed on Mar. 12, 2017.

(51) Int. Cl.
| | |
|---|---|
| *C07F 9/40* | (2006.01) |
| *C07D 225/08* | (2006.01) |
| *C12N 9/00* | (2006.01) |
| *B82Y 30/00* | (2011.01) |

(52) U.S. Cl.
CPC .......... *C07F 9/4071* (2013.01); *C07D 225/08* (2013.01); *C12N 9/93* (2013.01); *B82Y 30/00* (2013.01); *C12N 2310/351* (2013.01); *C12N 2310/353* (2013.01); *C12N 2310/3527* (2013.01); *C12Y 605/01001* (2013.01)

(58) Field of Classification Search
CPC ........................... C07F 9/4071; C07D 225/08
See application file for complete search history.

(56) References Cited

PUBLICATIONS

Len et al., "Micellar Catalysis Using a Photochromic Surfactant: Application to the Pd-Catalyzed Tsuji-Trost Reaction in Water" J. Org. Chem., 79(2): 493-500 (2014).
Lu et al., "Carboxyl-polyethylene glycol-phosphoric acid: a ligand for highly stabilized iron oxide nanoparticles" J. Mater. Chem., 22:19806-19811 (2012).
Gnauck et al., "Carboxy-Terminated Oligo(ethylene glycol)—Alkane Phosphate: Synthesis and Self-Assembly on Titanium Oxide Surfaces" Langmuir 23(2):377-381 (2007).

*Primary Examiner* — Golam M Shameem
(74) *Attorney, Agent, or Firm* — McDonnell Boehnen Hulbert & Berghoff LLP

(57) ABSTRACT

Described herein is an enzyme-mediated approach to bioconjugation at nanoparticle (NP) surfaces. This process is enabled by a new synthetic linker compatible with the covalent attachment of alkyne modified substrates, including dyes, peptides and nucleic acids. The methods described herein specifically allow for the linkage of molecules to a DNA-functionalized nanoparticle surface. Enzymatic ligation of molecules to the terminal hydroxyl group of DNA using T4 DNA ligase is achieved through incorporation of a single monophosphate on the approaching substrate. In contrast to previous strategies, the linkers disclosed herein are compatible with alkyne modified molecules of a variety of sizes and charges indicating that the ligase minimally requires the monophosphate and the incoming hydroxyl for conjugation to be successful.

25 Claims, 16 Drawing Sheets
Specification includes a Sequence Listing.

Scheme 1: Monophosphate derivative

Scheme 1: Monophosphate derivative

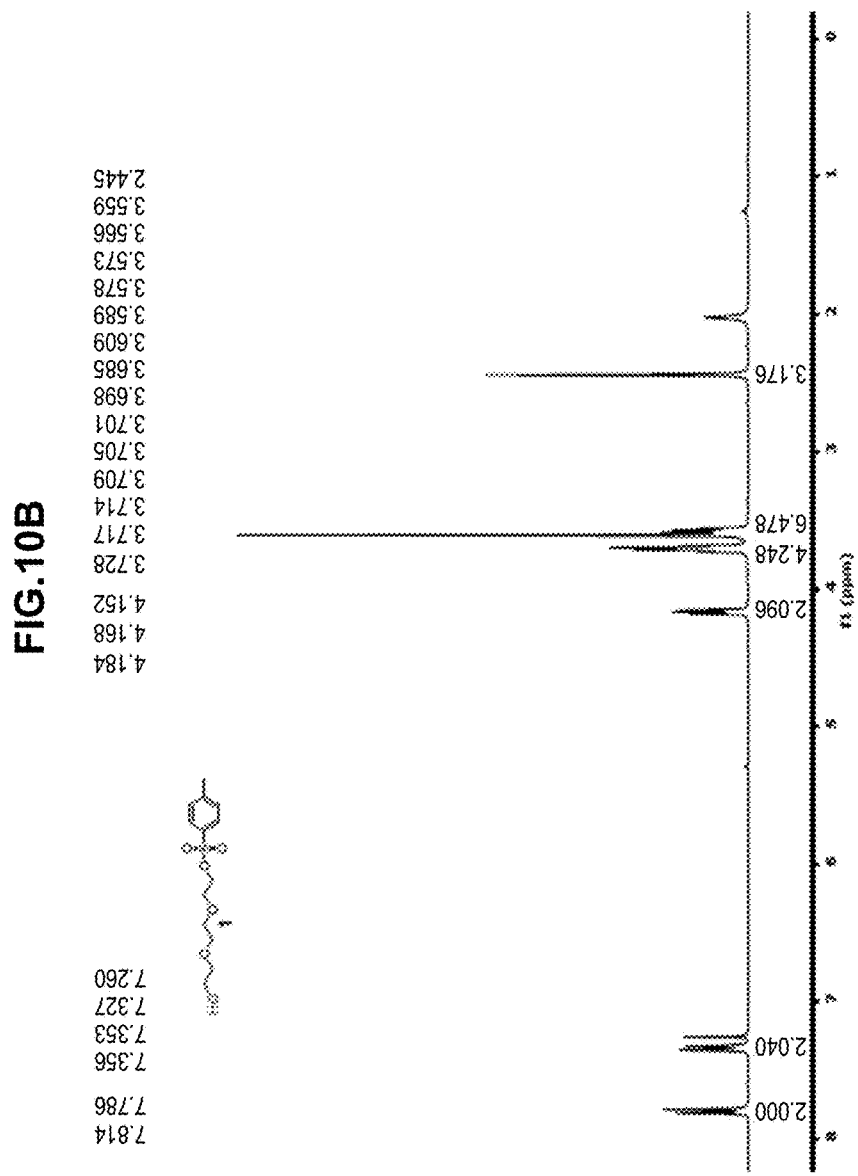

SEQUENCE LISTING

```
<160> NUMBER OF SEQ ID NOS: 8

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Cys Leu Pro Lys Thr Gly Gly Arg
1               5

<210> SEQ ID NO 2
<211> LENGTH: 22
<212> TYPE: DNA
<213> ORGANISM: Artificial Sequence
<220> FEATURE:
```

<223> OTHER INFORMATION: Synthetic

<400> SEQUENCE: 2
tttttttttt caatcacaac ca                                                    22

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
cgtcatcaac gatggttgtg attg                                                  24

<210> SEQ ID NO 4
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' linker

<400> SEQUENCE: 4
tcgttgatga cgctagctag ac                                                    22

<210> SEQ ID NO 5
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal alkylo

<400> SEQUENCE: 5

Cys Leu Pro Lys Thr Gly Gly Arg
1               5

<210> SEQ ID NO 6
<211> LENGTH: 12
<212> TYPE: PRT
<213> ORGANISM: Artificial Sequence
<220> FEATURE:
<223> OTHER INFORMATION: Synthetic

<400> SEQUENCE: 6

Cys Lys Arg Lys Lys Arg Arg Lys Arg Arg Arg Gly
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: N-terminal mono-phosphorylated (mp)

<400> SEQUENCE: 7

Cys Leu Pro Lys Thr Gly Gly Arg

```
<210> SEQ ID NO 8
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' mono-phosphorylated (mp) linker

<400> SEQUENCE: 8
tcgttgatga cgctagctag ac                                        22
```

UNIVERSAL ENZYME RESPONSIVE LINKER FOR ASSEMBLING LIGANDS ON DNA FUNCTIONALIZED NANOMATERIALS

CROSS-REFERENCE TO RELATED-APPLICATIONS

The present application claims priority to U.S. Provisional Patent Application No. 62/470,327 entitled "UNIVERSAL ENZYME RESPONSIVE LINKER FOR ASSEMBLING LIGANDS ON DNA FUNCTIONALIZED NANOMATERIALS" filed Mar. 12, 2017, which is incorporated by reference in its entirety.

SEQUENCE LISTING

The sequence listing submitted herewith, entitled: "16-1821-US_SequenceListing_ST25.txt" and 2 kb in size, is incorporated by reference in its entirety.

BACKGROUND

Surface functionalization of inorganic nanoparticles with DNA, RNA, peptides and dyes is needed for the assembly of nanoscale materials for a variety of applications ranging from biosensing, to bioimaging, and therapeutics. A critical step in building these hybrid biomaterials is the ability to present diverse chemical functionalities at a nanoparticles surface efficiently and in high enough yields to assemble diverse ligands. Chemical bioconjugation strategies, including the more common EDC approach for amide coupling and the use of thiol reactive linkers have been predominantly used for attaching peptides, dyes and nucleic acids to nanoparticles (NPs). This is attributed to their compatibility with aqueous conditions and their tolerance for higher salt concentrations that biomolecules often require to maintain their folded structures. However, such chemical conjugation strategies often require the pairing of a different chemical modification for each individual substrate to be attached to a NPs surface depending on the reactive sites available for functionalization.

In light of this multistep synthetic approach to nanoparticle functionalization, a generalized chemical approach was developed that is both biologically compatible and straightforward. A DNA functionalized NP (DNA-NP) was used as a platform on which to test the enzyme-mediated approach to nanoparticle functionalization. DNA-NPs have gained significant attention in the last two decades, owing to their ease of synthesis and chemical stability in aqueous environments. Hybridization-based assembly of nanomaterials takes advantage of the Watson-crick base pairing interactions of DNA's double helical structure.

To date there is no general enzymatic strategy for modification of the DNA on a DNA-nanoparticle to impart compatibility for chemical ligation between the DNA and a molecule of non-nucleic acid structure. The methods and compositions disclosed herein use the terminal ends of DNA molecules, in particular, the 3'OH end recognized by ligase enzymes. Disclosed herein are compositions that can interface chemical modifications with the specificity of the ligase. This versatile approach is important for the rapidly growing field of nucleic acid based therapeutics and offers an important strategy aimed at repurposing enzymes for use as assembly tools for functionalizing nanomaterials in a chemically specific manner.

SUMMARY

Disclosed herein are compositions and methods that enable functionalizing molecules with enzymes in an efficient manner (in contrast to multi-step synthetic chemical modification of biomolecules). Using the compositions and methods as disclosed herein, enzymes, with high specificity, can rapidly and covalently attach any alkyne, dibenzocyclooctyne group (DBCO) or other compatible "click" molecule onto DNA using T4 DNA ligase.

In one aspect, the disclosure is related to a heterobifunctional linker having the general formula: (HO)2(O)P-O-I-Y; wherein I is an intervening moiety, the intervening moiety having a molecular weight in the range of 100 to 10000; and Y is a chemically-reactive moiety, the chemically-reactive moiety being reactable to couple the linker to an organic compound in aqueous solution, or a salt thereof, the chemically-reactive moiety and intervening moieties being selected such that the heterobifunctional linker or salt thereof is water soluble at a concentration of at least 10 pM at a pH within the range of 6.5 to 7.8. In some embodiments, the chemically-reactive moiety is reactable to couple the linker to a biomolecule in aqueous solution.

In a second aspect, the disclosure relates to a composition comprising the heterobifunctional linker as disclosed herein, wherein the phosphate moiety of the heterobifunctional linker is covalently bound to a first molecule. In some embodiments, the first molecule is a nucleic acid, and the phosphate moiety of the heterobifunctional linker is covalently bound to a 3'-hydroxyl of a phosphate moiety of the nucleic acid to form a phosphodiester. In certain embodiments, the chemically-reactive moiety of the heterobifunctional linker is covalently bound to a second molecule.

In a third aspect, the disclosure relates to a composition comprising the heterobifunctional linker as disclosed herein, wherein the chemically-reactive moiety of the heterobifunctional linker is covalently bound to a second molecule.

In a fourth aspect, the disclosure relates to a method of covalently linking two molecules comprising:
  (a) reacting the chemically-reactive moiety of the heterobifunctional linker as disclosed herein with a first molecule comprising a functional group capable of covalently binding the chemically-reactive moiety of the heterobifunctional linker, wherein the reacting occurs under conditions and for a time suitable to covalently bind the first compound to the chemically-reactive moiety of the heterobifunctional linker; and
  (b) reacting the phosphate moiety of the heterobifunctional linker with a second molecule comprising a 3'-OH group of a nucleic acid phosphate in the presence of a T4 DNA ligase for a time and under conditions, to ligate the second molecule to the phosphate moiety of the first complex to form a phosphodiester bond between the nucleic acid phosphate and the phosphate moiety of the heterobifunctional linker.

In a fifth aspect, the disclosure relates to a kit comprising:
  (a) the heterobifunctional linker as disclosed herein;
  (b) reagents for reacting a first molecule to the reactive moiety of the heterobifunctional linker; and
  (c) a T4 DNA ligase and reagents to ligate a second molecule to the phosphate moiety of the heterobifunctional linker.

The present disclosure provides the following non-limiting numbered embodiments:

Embodiment 1: A heterobifunctional linker having the general formula:

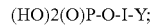

wherein
  I is an intervening moiety, the intervening moiety having a molecular weight in the range of 100 to 10000; and Y is a chemically-reactive moiety, the chemically-reactive moiety being reactable to couple the linker to an organic compound in aqueous solution,
or a salt thereof, the chemically-reactive moiety and intervening moieties being selected such that the heterobifunctional linker or salt thereof is water soluble at a concentration of at least 10 pM at a pH within the range of 6.5 to 7.8.

Embodiment 2: The heterobifunctional linker according to embodiment 1, wherein the chemically-reactive moiety is reactable to couple the linker to a biomolecule in aqueous solution.

Embodiment 3: The heterobifunctional linker according to embodiment 1 or embodiment 2, wherein the chemically-reactive moiety comprises an azide.

Embodiment 4: The heterobifunctional linker according to embodiment 1 or embodiment 2, wherein the chemically-reactive moiety comprises an alkyne.

Embodiment 5: The heterobifunctional linker according to embodiment 4, wherein the alkyne has the structural formula:

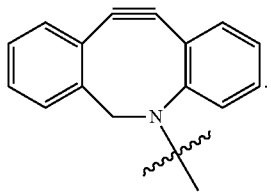 [SMILES: *N1Cc2ccccc2C#Cc2ccccc21]

Embodiment 6: The heterobifunctional linker according to embodiment 4, wherein the alkyne has the structural formula:

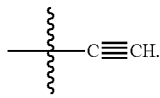

Embodiment 7: The heterobifunctional linker according to embodiment 1 or embodiment 2, wherein the chemically-reactive moiety comprises a maleimide.

Embodiment 8: The heterobifunctional linker according to embodiment 1 or embodiment 2, wherein the chemically-reactive moiety comprises a cyclopentadiene.

Embodiment 9: The heterobifunctional linker according to embodiment 1 or embodiment 2, wherein the chemically-reactive moiety comprises a thiol.

Embodiment 10: The heterobifunctional linker according to embodiment 1 or embodiment 2, wherein the chemically-reactive moiety comprises an alkene.

Embodiment 11: The heterobifunctional linker according to embodiment 10, wherein the chemically-reactive moiety is a terminal alkene.

Embodiment 12: The heterobifunctional linker according to embodiment 1 or embodiment 2, wherein the chemically-reactive moiety comprises a carboxylate.

Embodiment 13: The heterobifunctional linker according to embodiment 1 or embodiment 2, wherein the chemically-reactive moiety comprises an amine.

Embodiment 14: The heterobifunctional linker according to embodiment 1 or embodiment 2, wherein the chemically-reactive moiety comprises a carboxylate ester of N-hydroxysuccinimide.

Embodiment 15: The heterobifunctional linker according to embodiment 1 or embodiment 2, wherein the chemically-reactive moiety comprises an isocyanate or an isothiocyanate.

Embodiment 16: The heterobifunctional linker according to embodiment 1 or embodiment 2, wherein the chemically-reactive moiety comprises a maleimide, an iodoacetamide, a (pyridin-2-yl)disulfanyl, or a (3-carboxy-4-nitrophenyl)disulfanyl.

Embodiment 17: The heterobifunctional linker according to embodiment 1, wherein the chemically-reactive moiety is reactive in a cycloaddition, e.g., a 3+2 cycloaddition or a 4+2 cycloaddition, at a temperature below 60° C.

Embodiment 18: The heterobifunctional linker according to any of embodiments 1-17, wherein the intervening moiety comprises, consists essentially of, or is a polyethylene glycol.

Embodiment 19: The heterobifunctional linker according to embodiment 18, wherein the intervening moiety comprises, consists essentially of, or is a polyethyelene glycol having structure $—(CH_2CH_2O)_n—$ in which n is in the range of 3-200, e.g., 3-150, or 3-100, or 3-50, or 3-20, or 5-200, or 5-150, or 5-100, or 5-50, or 10-200, or 10-150, or 10-100.

Embodiment 20: The heterobifunctional linker according to embodiment 19, wherein the intervening moiety comprises the structure $—(CH_2CH_2O)_n—(CH_2)_m—$ in which m is in the range of 1-6, e.g., 2-6, or 1-4, or 2-4, or is 2 or 3.

Embodiment 21: The heterobifunctional linker according to any of embodiments 1-17, wherein the intervening moiety comprises, consists essentially of, or is a polyethylene imine.

Embodiment 22: The heterobifunctional linker according to embodiment 21, wherein the polyethyleneimine has a molecular weight in the range of 100-5000, e.g., 100-2000, or 100-1000, or 100-500, or 200-5000, or 200-2000, or 200-1000.

Embodiment 23: The heterobifunctional linker according to any of embodiments 1-17, wherein the intervening moiety comprises, consists essentially of, or is a copolymer or cooligomer of ethylene glycol and ethyleneimine, for example, having a molecular weight in the range of 100-5000, e.g., 100-2000, or 100-1000, or 100-500, or 200-5000, or 200-2000, or 200-1000.

Embodiment 24: The heterobifunctional linker according to any of embodiments 1-17, wherein the intervening moiety comprises, consists essentially of, or is a peptide oligomer or polypeptide, for example, having a molecular weight in the range of 100-5000, e.g., 100-2000, or 100-1000, or 100-500, or 200-5000, or 200-2000, or 200-1000.

Embodiment 25: The heterobifunctional linker according to any of embodiments 1-17, wherein the intervening moiety comprises, consists essentially of, or is a polyester of one or more of lactic acid and glycolic acid, for example, having a molecular weight in the range of 100-5000, e.g., 100-2000, or 100-1000, or 100-500, or 200-5000, or 200-2000, or 200-1000.

Embodiment 26: The heterobifunctional linker according to embodiment 25, wherein the intervening moiety comprises a polyester of one or more of lactic acid and glycolic acid, and wherein the polyester comprises poly(lactic acid-co-glycolic acid).

Embodiment 27: The heterobifunctional linker according to any of embodiments 1-17, wherein the intervening moiety comprises, consists essentially of, or is a poly(propylene glycol), for example, having a molecular weight in the range of 100-2000, 100-1000, or 100-500.

Embodiment 28: The heterobifunctional linker according to any of embodiments 1-17, wherein the intervening moiety comprises, consists essentially of, or is a poly(ethylene glycol-co-propylene glycol), for example, having a molecular weight in the range of 100-5000, e.g., 100-2000, or 100-1000, or 100-500, or 200-5000, or 200-2000, or 200-1000.

Embodiment 29: The heterobifunctional linker according to any of embodiments 1-28, wherein the intervening moiety comprises the structure -(L)-(CH$_2$)$_m$— in which m is in the range of 1-6, e.g., 2-6, or 1-4, or 2-4, or is 2 or 3 and in which L is a polyethylene glycol, a polyethylene imine, a copolymer or cooligomer of polyethylene glycol and polyethyleneimine, a peptide oligomer or polypeptide, a polyester of one or more of lactic acid and glycolic acid, a poly(propylene glycol), or a poly(ethylene glycol-co-propylene glycol).

Embodiment 30: The heterobifunctional linker according to any of embodiments 1-29, wherein there are no branched carbon atoms or nitrogen atoms within 4 atoms of, or within 6 atoms of, or within 8 atoms of, or within 10 atoms of the phosphate, a branched carbon atom or nitrogen atom being defined as having more than three non-hydrogen, non-carbonyl substituents directly bound thereto.

Embodiment 31: The heterobifunctional linker according to any of embodiments 1-30, wherein the heterobifunctional linker has a molecular weight in the range of 100-7000, or 100-5000, or 100-2000, or 100-1000, or 100-500, or 200-10000, or 200-7000, or 200-5000, or 200-2000, or 200-1000, or 200-500, or 500-10000, or 500-7000, or 500-5000, or 500-2000, or 1000-10000, or 1000-7000, or 1000-5000.

Embodiment 32: The heterobifunctional linker according to embodiment 1, having the structure:

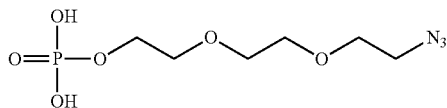 [SMILES: [N-]=[N+]=NCCOCCOCCOP(=O)(O)O]

Embodiment 33: A composition comprising the heterobifunctional linker of any one of embodiments 1-32, wherein the phosphate moiety of the heterobifunctional linker is covalently bound to a first molecule.

Embodiment 34: The composition according to embodiment 33, wherein the first molecule comprises a nucleic acid, and wherein the phosphate moiety of the heterobifunctional linker is covalently bound to a 3'-hydroxyl of a phosphate moiety of the nucleic acid to form a phosphodiester.

Embodiment 35: The composition according to embodiment 34, wherein the nucleic acid is a DNA of a DNA-coated nanoparticle.

Embodiment 36: A composition according to any of embodiments 33-35, wherein the reactive moiety of the heterobifunctional linker is covalently bound to a second molecule.

Embodiment 37: A composition comprising the heterobifunctional linker of any one of embodiments 1-32, wherein the chemically-reactive moiety of the heterobifunctional linker is covalently bound to a second molecule.

Embodiment 38: A composition according to embodiment 36 or embodiment 37, wherein the second molecule is, comprises, or consists essentially of a polypeptide, such as a protein.

Embodiment 39: A composition according to embodiment 36 or embodiment 37, wherein the second molecule is, comprises or consists essentially of a nucleic acid, such as a DNA or an RNA.

Embodiment 40: A composition according to embodiment 36 or embodiment 37, wherein the second molecule is, comprises, or consists essentially of a dye.

Embodiment 41: A composition according to embodiment 36 or embodiment 37, wherein the second molecule comprise a lipid, a sterol, fatty acids, or a polymer.

Embodiment 42: A composition according to any of embodiments 36-41, wherein the chemically-reactive moiety of the heterobifunctional linker comprises an azide, and the heterobifunctional linker is covalently bound to the second molecule through a thiazole formed from the azide and an alkyne.

Embodiment 43: A composition according to any of embodiments 36-41, wherein the chemically-reactive moiety of the heterobifunctional linker comprises an alkyne, and the heterobifunctional linker is covalently bound to the second molecule through a thiazole formed from the alkyne and an azide.

Embodiment 44: A composition according to any of embodiments 36-41, wherein the chemically-reactive moiety of the heterobifunctional linker comprise a cyclopentadiene, and the heterobifunctional linker is covalently bound to the second molecule through a cycloaddition product of the cyclopentadiene.

Embodiment 45: A composition according to any of embodiments 36-41, wherein the chemically-reactive moiety of the heterobifunctional linker comprise a thiol, and the heterobifunctional linker is covalently bound to the second molecule through a thiol-ene or thiol-yne reaction product of the thiol.

Embodiment 46: A composition according to any of embodiments 36-41, wherein the chemically-reactive moiety of the heterobifunctional linker comprises an alkene, e.g., a terminal alkene, and the heterobifunctional linker is covalently bound to the second molecule through a thiol-ene reaction product of the alkene.

Embodiment 47: A composition according to any of embodiments 36-41, wherein the chemically-reactive moiety of the heterobifunctional linker comprise a maleimide, and the heterobifunctional linker is covalently bound to the second molecule through a thiol-ene reaction product of the maleimide.

Embodiment 48: A composition according to any of embodiments 36-41, wherein the chemically-reactive moiety of the heterobifunctional linker comprises an alkyne, e.g., a terminal alkyne, and the heterobifunctional linker is covalently bound to the second molecule through a thiol-ene reaction product of the alkyne.

Embodiment 49: A composition according to any of embodiments 36-41, wherein the chemically-reactive moiety of the heterobifunctional linker comprise a carboxylate and the heterobifunctional linker is covalently bound to the second molecule through a condensation reaction product of the carboxylate (e.g., with an amine to form an amide).

Embodiment 50: A composition according to any of embodiments 36-41, wherein the chemically-reactive moiety of the heterobifunctional linker comprises an and the heterobifunctional linker is covalently bound to the second molecule through a condensation reaction product of the amine (e.g., with a carboxylate to form an amide).

Embodiment 51: A composition according to any of embodiments 36-41, wherein the chemically-reactive moiety of the heterobifunctional linker comprise a carboxylate ester of N-hydroxysuccinimide and the heterobifunctional linker is covalently bound to the second molecule through a condensation reaction product of the a carboxylate ester of N-hydroxysuccinimide (e.g., with an amine to form an amide).

Embodiment 52: A composition according to any of embodiments 36-41, wherein the chemically-reactive moiety of the heterobifunctional linker comprises an isocyanate or an isothiocyanate and the heterobifunctional linker is covalently bound to the second molecule through a reaction product of the isocyanate or isothiocyanate (e.g., with an amine such as a lysine amine to form a urea or a thiourea).

Embodiment 53: A composition according to any of embodiments 36-41, wherein the chemically-reactive moiety of the heterobifunctional linker comprises an iodoacetamide and the heterobifunctional linker is covalently bound to the second molecule through a reaction product of the iodoacetamide (e.g., with a thiol such as a cysteine thiol to form a thioether).

Embodiment 54: A composition according to any of embodiments 36-41, wherein the chemically-reactive moiety of the heterobifunctional linker comprise a (pyridin-2-yl)disulfanyl or a (3-carboxy-4-nitrophenyl)disulfanyl and the heterobifunctional linker is covalently bound to the second molecule through a reaction product of the (pyridin-2-yl)disulfanyl or (3-carboxy-4-nitrophenyl)disulfanyl iodoacetamide (e.g., with a thiol such as a cysteine thiol to form a disulfide bridge).

Embodiment 55: A composition according to any of embodiments 36-41, wherein the chemically-reactive moiety of the heterobifunctional linker is reactive in a cycloaddition (e.g., a [3+2] cycloaddition or a [4+2] cycloaddition) at a temperature below 60° C., and the heterobifunctional linker is covalently bound to the second molecule through a cycloaddition reaction product of the chemically-reactive moiety.

Embodiment 56: A method of covalently linking two molecules (e.g., to form a composition according to any of embodiments 36 and 38-55) comprising:
 (a) reacting the chemically-reactive moiety of the heterobifunctional linker of any of claims 1-21 with a first molecule comprising a functional group capable of covalently binding the chemically-reactive moiety of the heterobifunctional linker, wherein the reacting occurs under conditions and for a time suitable to covalently bind the first compound to the chemically-reactive moiety of the heterobifunctional linker; and
 (b) reacting the phosphate moiety of the heterobifunctional linker with a second molecule comprising a 3'-OH group of a nucleic acid phosphate in the presence of a T4 DNA ligase for a time and under conditions, to ligate the second molecule to the phosphate moiety of the first complex to form a phosphodiester bond between the nucleic acid phosphate and the phosphate moiety of the heterobifunctional linker.

Embodiment 57: The method of embodiment 56, wherein step (a) is performed before step (b).

Embodiment 58: The method of embodiment 57, wherein the product of step (a) is purified (e.g., using chromatography) before step (b) is performed.

Embodiment 59: The method of any of embodiments 56-58, wherein step (a) is performed using copper catalysis.

Embodiment 60: A kit comprising:
 (a) the heterobifunctional linker of any of embodiments 1-32;
 (b) reagents for reacting a first molecule to the reactive moiety of the heterobifunctional linker; and
 (c) a T4 DNA ligase and reagents to ligate a second molecule to the phosphate moiety of the heterobifunctional linker.

These and other features and advantages of the present disclosure will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following figures are in accordance with example embodiments.

FIG. 10B shows the $^1$H NMR 300 of compound 1 CDCl$_3$.

DETAILED DESCRIPTION

Figure 1:
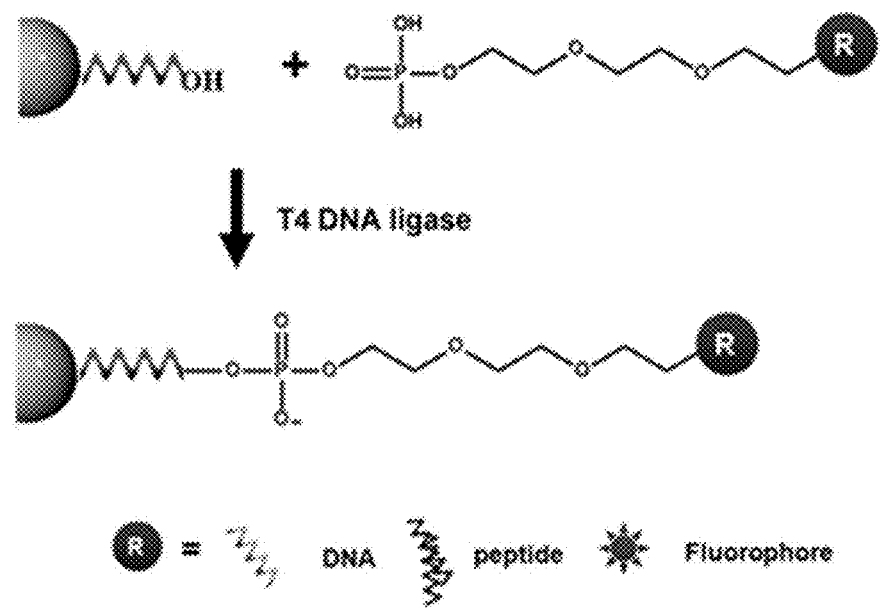
FIG. 1 shows a schematic representation of the heterobifunctional linker that presents an azide for copper catalyzed click chemistry and a monophosphate for enzymatic ligation.

The heterobifunctional linkers described here allow the ability to enzymatically attach, for example, a nucleic acid molecule to a diverse range of molecules or nanomaterials (these include but are not limited to: peptides, enzymes, antibodies, dyes, nucleic acids) with various chemical modifications through a single heterobiofunctional linker. These linkers, for example, present an azide on one end for utilizing the copper catalyzed alkyne-azide cycloaddition (CuAAC) "click" chemistry approach and at the other end a terminal phosphate moiety for ligation to the 3' hydroxyl of a DNA molecule by the T4 DNA ligase enzyme. This is advantageous as it opens the door to a variety of chemical modifications through a single robust enzyme approach.

For example, the heterobifunctional linkers disclosed herein can be used for the selective functionalization of DNA-coated nanoparticles (NPs). DNA functionalized materials are an extremely attractive platform for drug delivery applications, biosensing and bioimaging. Using DNA which presents a terminal 3' hydroxyl DNA can be functionalized using T4 DNA ligase, ATP, and the monophosphorylated heterobiofunctional linker described herein to obtain the covalent attachment of the molecule of interest to DNA under mild, biocompatible conditions. This linker can accelerate the surface modification of substrate-based technologies as well (e.g., the selective, efficient assembly of biomolecules on a chemically modified surface). For example, an alkyne modified peptide can be "clicked" to the heterobifunctional linker disclosed herein and then enzymatically attached to DNA linkers affixed to either a nanoparticle surface or a substrate using T4 DNA ligase.

The DNA functionalized nanomaterial is used as an example substrate, but could be replaced by any kind of chip assay or substrate to which DNA is attached at its 5' end to the surface. The results show that the minimal requirements for the success of the linker to attach an R ground (where R can be DNA, peptide or dye/fluorophore) using the linker to a DNA molecule is the presence of the monophosphate group bound to a flexible intervening moiety (for example, triethylene glycol).

In one aspect, the disclosure is related to a heterobifunctional linker having the general formula: (HO)2(O)P-O-I-Y; wherein I is an intervening moiety, the intervening moiety having a molecular weight in the range of 100 to 10000; and Y is a chemically-reactive moiety, the chemically-reactive moiety being reactable to couple the linker to an organic compound in aqueous solution, or a salt thereof, the chemically-reactive moiety and intervening moiety being selected such that the heterobifunctional linker or salt thereof is water soluble at a concentration of at least 10 pM at a pH within the range of 6.5 to 7.8.

As used herein, the term "chemically-reactive moiety" refers to any moiety that is reactable to covalently couple the linker to an organic compound. For covalent attachment, the chemistry should be compatible with terminal amines or carboxylic acids when considering the attachment of a peptide to the hydroxyl or phosphate groups of nucleic acid molecule. As the reactive chemistry for DNA is limited, typically DNA is first modified with a chemical leaving group that would make its attachment to the peptide suitable with chemistries such as ethyl(dimethylaminopropyl) carbodiimide, N-hydroxysuccinimide (EDC-NHS) coupling chemistry or thiol reactive chemistry.

The chemically reactive moiety can be, for example, a moiety that can participate in a so-called "click" reaction. Click reactions are known to be reactions that are high yielding, wide in scope, create only byproducts that can be removed without chromatography, are simple to perform, and can be conducted in easily removable or benign solvents. While a variety of such chemistries are described below, the person of ordinary skill in the art will appreciate that other chemistries can be adapted for use in the systems described herein.

In some embodiments, the chemically-reactive moiety is reactable to couple the linker to a biomolecule in aqueous solution. In certain embodiments, the chemically-reactive moiety comprises an azide. In an embodiment, the chemically-reactive moiety comprises an alkyne (e.g., a strained alkyne such as an alkyne in a ring), for example, having has the structural formula:

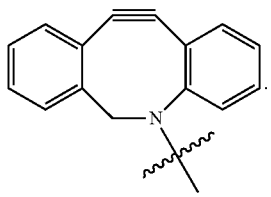 [SMILES: *N1Cc2ccccc2C#Cc2ccccc21]

In another embodiment, the alkyne has the structural formula:

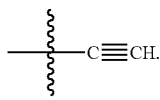

In some embodiments of the heterobifunctional linker, the chemically-reactive moiety comprises a molecule selected from the group consisting of an alkene, an amine, a maleimide, a carboxylate, a carboxylate ester of N-hydroxysuccinimide, a (3-carboxy-4-nitrophenyl)disulfanyl, a cyclopentadiene, an iodoacetamide, an isocyanate, isothiocyanate, a (pyridin-2-yl)disulfanyl, and a thiol. In an embodiment, the chemically-reactive moiety comprises an alkene and the alkene is a terminal alkene.

In some embodiments of the heterobifunctional linker, the chemically-reactive moiety is reactive in a cycloaddition at a temperature below 60° C. In non-limiting examples, the cycloaddition is a [3+2] cycloaddition or a [4+2] cycloaddition.

As used herein, the term "intervening moiety" refers to any structure or molecule that joins phosphate moiety of heterobifunctional linker to the chemically-reactive moiety. Such an intervening moiety or moieties can also be referred to as a bridge, or a spacer, moiety or moieties. In some embodiments, the intervening moiety comprises an entity selected from the group consisting of a polyethylene glycol, a polyethyleneimine, a copolymer or cooligomer of ethylene glycol and ethyleneimine, a peptide oligomer or polypeptide, a polyester of one or more of lactic acid and glycolic acid, a poly(propylene glycol), and a poly(ethylene glycol-co-propylene glycol).

In certain embodiments, the intervening moiety comprises a polyethyelene glycol having structure —(CH$_2$CH$_2$O)$_n$— in which n is in the range of 3-200. In some embodiments, n is in the range of 3-150, or 3-100, or 3-50, or 3-20, or 5-200, or 5-150, or 5-100, or 5-50, or 10-200, or 10-150, or 10-100. In an embodiment, the intervening moiety comprises the structure —(CH$_2$CH$_2$O)$_n$—(CH$_2$)$_m$— in which m is in the range of 1-6 (for example, m is in the range of 2-6, or 1-4, or 2-4, or m is 2 or 3).

In certain embodiments, the intervening moiety comprises, consists essentially of, or is a polyethylene imine, and the polyethyleneimine can have a molecular weight in the range of 100-5000, for example, 100-2000, or 100-1000, or 100-500, or 200-5000, or 200-2000, or 200-1000.

In some embodiments, the intervening moiety comprises, consists essentially of, or is a copolymer or cooligomer of ethylene glycol and ethyleneimine, for example, having a molecular weight in the range of 100-5000, for example, 100-2000, or 100-1000, or 100-500, or 200-5000, or 200-2000, or 200-1000.

In certain embodiments, the intervening moiety comprises, consists essentially of, or is a peptide oligomer or polypeptide, for example, having a molecular weight in the range of 100-5000, for example, 100-2000, or 100-1000, or 100-500, or 200-5000, or 200-2000, or 200-1000. The peptide oligomer or polypeptide can be formed from, for example, natural amino acids, unnatural amino acids, or a combination thereof. In certain embodiments, the peptide oligomer or polypeptide is formed from natural L-amino acids. In other embodiments, the peptide oligomer or polypeptide is formed from D-amino acids (e.g., enantiomers of natural L-amino acids) or from a combination of D- and L-amino acids.

In some embodiments, the intervening moiety comprises, consists essentially of, or is a polyester of one or more of lactic acid and glycolic acid, for example, having a molecular weight in the range of 100-5000, for example, 100-2000, or 100-1000, or 100-500, or 200-5000, or 200-2000, or 200-1000. In some embodiments, the polyester is poly(lactic acid-co-glycolic acid).

In certain embodiments, the intervening moiety comprises, consists essentially of, or is a poly(propylene glycol), for example, having a molecular weight in the range of 100-2000, 100-1000, or 100-500.

In some embodiments, the intervening moiety comprises, consists essentially of, or is a poly(ethylene glycol-co-propylene glycol), for example, having a molecular weight in the range of 100-5000, for example, 100-2000, or 100-1000, or 100-500, or 200-5000, or 200-2000, or 200-1000.

In an embodiment, the intervening moiety comprises the structure -(L)-(CH$_2$)$_m$— in which m is in the range of 1-6 (e.g., 2-6, or 1-4, or 2-4, or is 2 or 3), and in which L comprises a polyethylene glycol, a polyethyleneimine, a copolymer or cooligomer of polyethylene glycol and polyethyleneimine, a peptide oligomer or polypeptide, a polyester of one or more of lactic acid and glycolic acid, a poly(propylene glycol), or a poly(ethylene glycol-co-propylene glycol).

In some embodiments of the heterobifunctional linker as disclosed herein, there are no branched carbon atoms or nitrogen atoms within 4 atoms of, or within 6 atoms of, or within 8 atoms of, or within 10 atoms of the phosphate, a branched carbon atom or nitrogen atom being defined as having more than three non-hydrogen, non-carbonyl substituents directly bound thereto.

In certain embodiments, the heterobifunctional linker has a molecular weight in the range of 100-10000. For example, the heterobifunctional linker can have a molecular weight in the range of 100-7000, or 100-5000, or 100-2000, or 100-1000, or 100-500, or 200-10000, or 200-7000, or 200-5000, or 200-2000, or 200-1000, or 200-500, or 500-10000, or 500-7000, or 500-5000, or 500-2000, or 1000-10000, or 1000-7000, or 1000-5000.

The term "molecular weight", as used herein, generally refers to the mass or average mass of any of the compositions disclosed herein (e.g. the heterobifunctional linker, the intervening moiety, the chemically-reactive moiety, or any of the entities or molecules comprising the linkers and moieties described herein). The molecular weight of any of the materials disclosed herein may be calculated as the sum of the atomic weight of each atom in the formula of the material multiplied by the number of each atom, and all molecular weights disclosed herein are provided as weight average molecular weights. It may also be measured by mass spectrometry, NMR, chromatography, light scattering, viscosity, and/or any other methods known in the art. Relative atomic and molecular mass values are dimensionless, but can be given the "unit" Dalton (or atomic mass unit) to indicate that the number is equal to the mass of one molecule divided by $1/12$ of the mass of one atom of $^{12}C$. It is known in the art that the unit of molecular weight may be g/mol, Dalton (Da), or atomic mass unit (amu), wherein 1 g/mol=1 Da=1 amu.

In an embodiment, the heterobifunctional linker as disclosed herein has the structure:

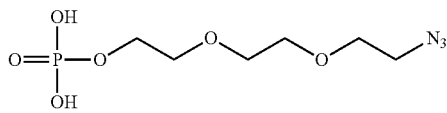 [SMILES: [N-]=[N+]=NCCOCCOCCOP(=O)(O)O]

In a second aspect, the disclosure relates to a composition comprising the heterobifunctional linker as disclosed herein, wherein the phosphate moiety of the heterobifunctional linker is covalently bound to a first molecule. In some embodiments, the first molecule comprises a nucleic acid, and the phosphate moiety of the heterobifunctional linker is covalently bound to a 3'-hydroxyl of a phosphate moiety of the nucleic acid to form a phosphodiester. In some embodiments, the nucleic acid contemplated comprises about 5 to about 150, or more nucleotides in length. For example, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, about 400 to about 10,000 nucleotides or more in length, and all nucleic acids intermediate in length of the sizes specifically disclosed to the extent that the nucleic acid is able to achieve the desired result. Accordingly, nucleic acids of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated. In an embodiment, the nucleic acid comprises DNA of a DNA-coated nanoparticle. In certain embodiments of the second aspect, the chemically-reactive moiety of the heterobifunctional linker is covalently bound to a second molecule.

In a third aspect, the disclosure relates to a composition comprising the heterobifunctional as disclosed herein, wherein the chemically-reactive moiety of the heterobifunctional linker is covalently bound to a second molecule.

In some embodiments of the second or third aspects, the second molecule is, comprises, or consists essentially of a polypeptide, a nucleic acid (such as DNA or RNA), a dye, a lipid, a sterol, a fatty acid, and a polymer. For example, the heterobiofunctional linker described herein, allows one the ability to enzymatically attach a nucleic acid molecule to a diverse range of molecules including, but not limited to, peptides, enzymes, antibody complexes, conjugates, natural ligands, small molecules, quantum dots, radioactive isotopes or chelates thereof, cytokines, pro-apoptotic substances, pore forming substances, fluorescent proteins (such as green fluorescent protein (GFP, EGFP), blue fluorescent protein (EBFP, EBFP2), cyan fluorescent protein (ECFP, Cerulean, CyPet) and yellow fluorescent protein derivatives (YFP, Citrine, Venus, YPet), monoclonal antibodies, polyclonal antibodies, bifunctional antibodies, dyes, aromatic dyes, fluorophores, fluorescein, rhodamine, cyanine dyes Cy dyes (such as Cy3, Cy5, and the like, or the Alexa™ family of dyes (such as Alexa 488, 500, 514, 532, 546, 555, 568, 594, 610, 633, 647, 660, 680, 700, and 750), nucleic acids, DNA, RNA, aptamers, drugs (e.g., cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™), cyclophosphamide); aromatase combinations; ara-C, adriamycin, cytoxan, gemcitabine, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine), prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins Depending on the particular chemistry used, the chemically-reactive moiety of the linker can react with a moiety that is considered part of the second molecule, e.g., a thiol of a peptide, or rather with a moiety that is provided on the second molecule specifically for the purpose of attachment, e.g., an alkyne or an azide functionalized onto a nucleic acid to provide for an alkyne-azide click reaction.

In certain embodiments of the second aspect,
(a) the chemically-reactive moiety of the heterobifunctional linker comprises an azide, and the heterobifunctional linker is covalently bound to the second molecule through a thiazole formed from the azide and an alkyne;
(b) the chemically-reactive moiety of the heterobifunctional linker comprises an alkyne, and the heterobifunctional linker is covalently bound to the second molecule through a thiazole formed from the alkyne and an azide;
(c) the chemically-reactive moiety of the heterobifunctional linker comprises a cyclopentadiene, and the heterobifunctional linker is covalently bound to the second molecule through a cycloaddition product of the cyclopentadiene;
(d) the chemically-reactive moiety of the heterobifunctional linker comprises a thiol, and the heterobifunctional linker is covalently bound to the second molecule through a thiol-ene or thiol-yne reaction product of the thiol;
(e) the chemically-reactive moiety of the heterobifunctional linker comprises an alkene (for example, a terminal alkene), and the heterobifunctional linker is covalently bound to the second molecule through a thiol-ene reaction product of the alkene;
(f) the chemically-reactive moiety of the heterobifunctional linker comprises a maleimide, and the heterobifunctional linker is covalently bound to the second molecule through a thiol-ene reaction product of the maleimide;
(g) the chemically-reactive moiety of the heterobifunctional linker comprises an alkyne (for example, a terminal alkyne), and the heterobifunctional linker is covalently bound to the second molecule through a thiol-ene reaction product of the alkyne;
(h) the chemically-reactive moiety of the heterobifunctional linker comprises a carboxylate and the heterobifunctional linker is covalently bound to the second molecule through a condensation reaction product of the carboxylate (for example, with an amine to form an amide);
(i) the chemically-reactive moiety of the heterobifunctional linker comprises an amine and the heterobifunctional linker is covalently bound to the second molecule through a condensation reaction product of the amine (for example, with a carboxylate to form an amide);
(j) the chemically-reactive moiety of the heterobifunctional linker comprises a carboxylate ester of N-hydroxysuccinimide and the heterobifunctional linker is covalently bound to the second molecule through a condensation reaction product of the a carboxylate ester of N-hydroxysuccinimide (for example, with an amine to form an amide);
(k) the chemically-reactive moiety of the heterobifunctional linker comprises an isocyanate or an isothiocyanate and the heterobifunctional linker is covalently bound to the second molecule through a reaction product of the isocyanate or isothiocyanate (for example, with an amine such as a lysine amine to form a urea or a thiourea);
(l) the chemically-reactive moiety of the heterobifunctional linker comprises an iodoacetamide and the heterobifunctional linker is covalently bound to the second molecule through a reaction product of the iodoacetamide (for example, with a thiol such as a cysteine thiol to form a thioether); or
(m) the chemically-reactive moiety of the heterobifunctional linker comprises a (pyridin-2-yl)disulfanyl or a (3-carboxy-4-nitrophenyl)disulfanyl and the heterobifunctional linker is covalently bound to the second molecule through a reaction product of the (pyridin-2-yl)disulfanyl or (3-carboxy-4-nitrophenyl)disulfanyl iodoacetamide (for example, with a thiol such as a cysteine thiol to form a disulfide bridge).

In some embodiments of the second or third aspects, the chemically-reactive moiety of the heterobifunctional linker is reactive in a cycloaddition (e.g., a [3+2] cycloaddition or a [4+2] cycloaddition) at a temperature below 60° C., and the heterobifunctional linker is covalently bound to the second molecule through a cycloaddition reaction product of the chemically-reactive moiety.

In a fourth aspect, the disclosure relates to a method (e.g., to form a composition) of covalently linking two molecules comprising:
(a) reacting the chemically-reactive moiety of the heterobifunctional linker as disclosed herein with a first molecule comprising a functional group capable of covalently binding the chemically-reactive moiety of the heterobifunctional linker, wherein the reacting occurs under conditions and for a time suitable to covalently bind the first compound to the chemically-reactive moiety of the heterobifunctional linker; and
(b) reacting the phosphate moiety of the heterobifunctional linker with a second molecule comprising a 3'-OH group of a nucleic acid phosphate in the presence of a T4 DNA ligase for a time and under conditions, to ligate the second molecule to the phosphate moiety of the first complex to form a phosphodiester bond between the nucleic acid phosphate and the phosphate moiety of the heterobifunctional linker.

In some embodiments of the fourth aspect, step (a) is performed before step (b). In an embodiments, the product of step (a) is purified (e.g., using chromatography) before step (b) is performed. In certain embodiments, step (a) is performed using copper catalysis.

In a fifth aspect, the disclosure relates to a kit comprising:
(a) the heterobifunctional linker as disclosed herein;
(b) reagents for reacting a first molecule to the reactive moiety of the heterobifunctional linker; and
(c) a T4 DNA ligase and reagents to ligate a second molecule to the phosphate moiety of the heterobifunctional linker.

Optimal amounts of kit reagents to be used in a given reaction can be readily determined by the skilled artisan having the benefit of the current disclosure. The kits, typically, can be adopted to contain the constituents aforedescribed in separate packaging or compartments.

When a structure is described as consisting essentially of a particular moiety, at least 70%, at least 80%, or even at least 90%, of that structure by weight is made up of that moiety. The structure can additionally include, for example, a linker disposed between that particular moiety and a reactive group.

EXAMPLES

Example 1

Universal Enzyme Responsive Linker for Assembling Ligands on DNA Functionalized Nanomaterials Enzymatic chemical ligations are a powerful tool by which two DNA ends, one bearing a 3' hydroxyl group and the other bearing a 5' monophosphate group, can be brought together by covalent attachment to form a new phosphodiester bond. DNA ligase is utilized for attaching DNA primers and templates to DNA functionalized substrates for DNA microarray and sequencing applications. To date there is no general enzymatic strategy for modification of the DNA on a DNA-nanoparticle to impart compatibility for chemical ligation between the DNA and a molecule of non-nucleic acid structure.

Disclosed herein, is a method that utilizes an enzyme-responsive auxiliary monophosphate cross linker to universally ligate a diverse array of molecules of interest to the DNA on a DNA-nanoparticle scaffold (see FIG. 1).

This approach was developed to address the need for a quick, robust and scalable way to attach biomolecules and other small molecule tags to nanoparticle surfaces without the need for multistep synthesis. The examples provided herein demonstrate that this can be achieved under aqueous, physiologically relevant conditions to address many of these desired qualities. The ability of the ligase to covalently attach a variety of molecules (i.e. planar, hydrophobic, hydrophilic, charged) shows the enormous potential and versatility of this approach.

Figure 2:
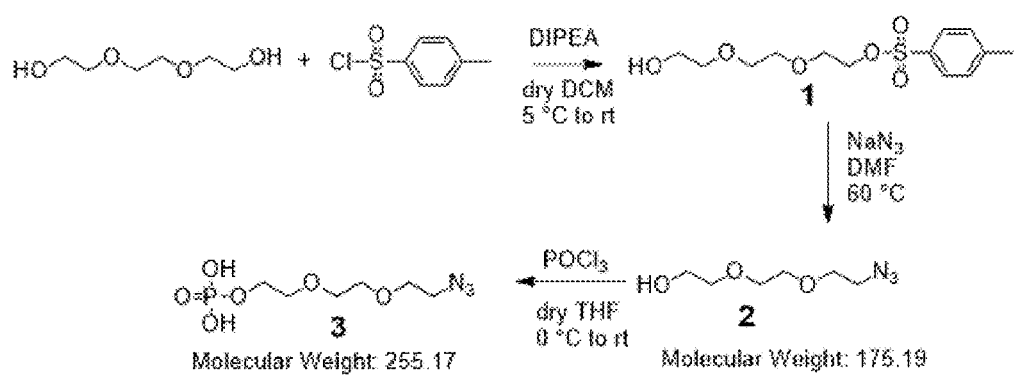
FIG. 2 shows an exemplary four step synthesis from commercially available reagents that results in a monophosphorylated linker and an azide group that can be used for copper catalyzed click reactions.

A major objective in the design of the heterobifunctional linker was to interface nucleic acids with a variety of important moieties relevant for biosensing and therapeutic applications. The four-step synthesis from commercially available reagents results in a monophosphorylated linker and an azide group that can be used for copper catalyzed "click" reactions (see FIG. 2). It was of interest to sample key molecules relevant to diagnostics and therapeutics and therefore a Cy3 fluorophore, a cell penetrating peptide, and a second nucleic acid were all evaluated for their ability to efficiently ligate to the linker.

Figure 3:
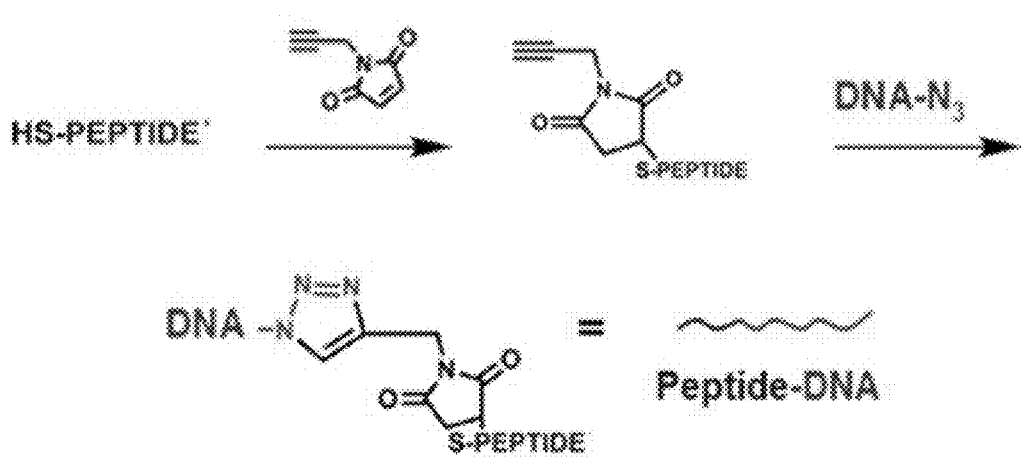
FIG. 3 shows alkyne modification of peptides. Alkyne modification allows for covalent attachment of a peptide to the monophosphorylated linker. Once purified, the alkyne modified peptide can be attached to the azide of the monophosphorylated linker forming the tetrazole linkage.

The approach relies on the ability to engage the active site of the ligase and allow space to tether larger molecules such as dyes onto the linker while achieving sufficient ligation efficiencies. In order to evaluate the extent of ligation on a DNA-nanoparticle surface a combination of dynamic light scattering, agarose gel electrophoresis and fluorescence spectroscopy were utilized. In each instance the molecule of interest (dye, peptide, or DNA) was first covalently linked to the monophosphate linker using standard copper catalyzed click conditions. Following purification, the molecules were then incubated with a DNA-functionalized nanoparticle in presence of sufficient ATP and T4 DNA ligase. Phosphorylated TAT peptide (CKRKKRRKRRRG; SEQ ID NO:06) was of interest to generate and ligate to the particle surface as TAT peptide is known to cross the lipid bilayer of a cell due to its high amount of positively charged amino acid residues. In order to attach a clickable group to the TAT peptide it was synthesized with a terminal cysteine residue to which a maleimide-alkyne was used to drive a Michael-Addition of the alkyne to the peptide's amino end. (see FIG. 3)

Figure 4A:
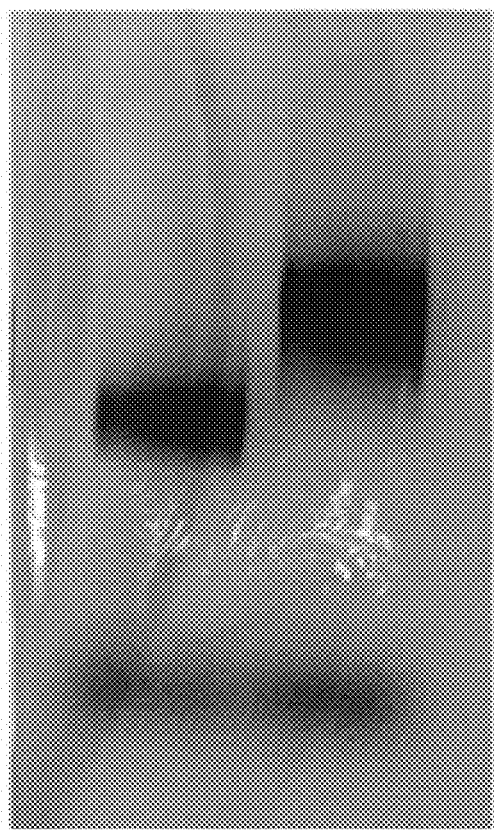
FIG. 4A shows an exemplary size and charge analysis of the products generated through covalent enzymatic attachment. An agarose gel shift assay demonstrates the successful linkage of a short peptide (CLPKTGGR; SEQ ID NO:01) to the surface of a gold nanoparticle.
Figure 4B:
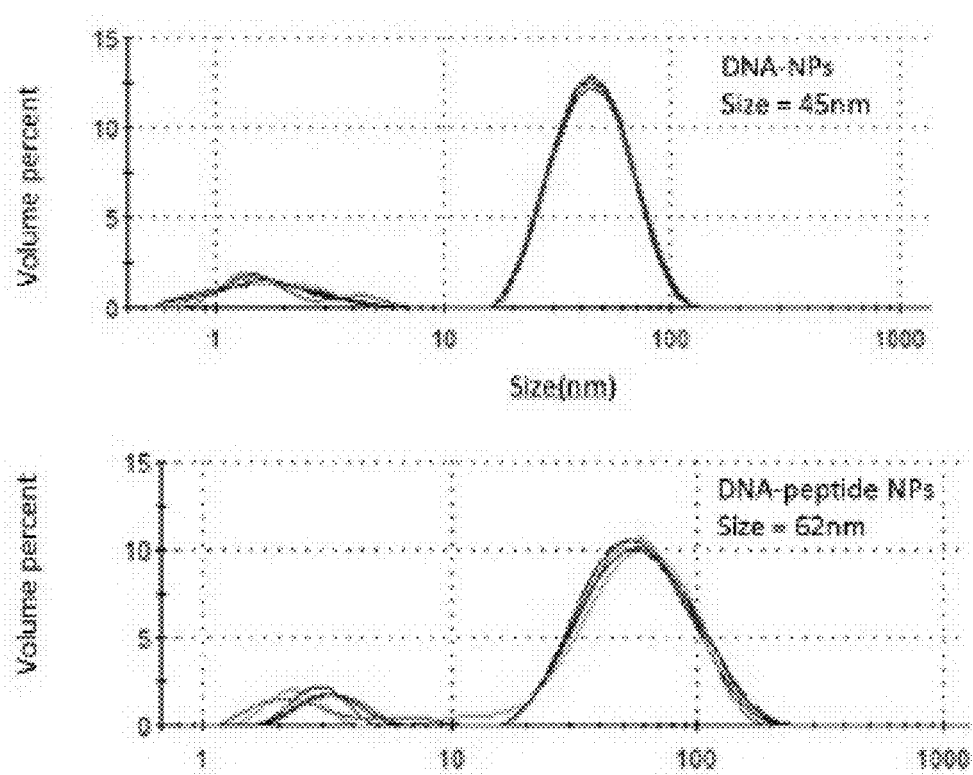
FIG. 4B shows an exemplary size and charge analysis of the products generated through covalent enzymatic attachment. A dynamic light scattering analysis of the peptide conjugated gold nanoparticle demonstrates an increase in overall size of the particles.

The alkyne modification allowed for covalent attachment of the peptide to the monophosphorylated linker. Once purified, the alkyne modified peptide is attached to the azide of the monophosphorylated linker forming the tetrazole linkage. The characterization of the particles post ligation with the linker modified peptide at the DNA-NP surface is shown in FIG. 4.

Figure 5:
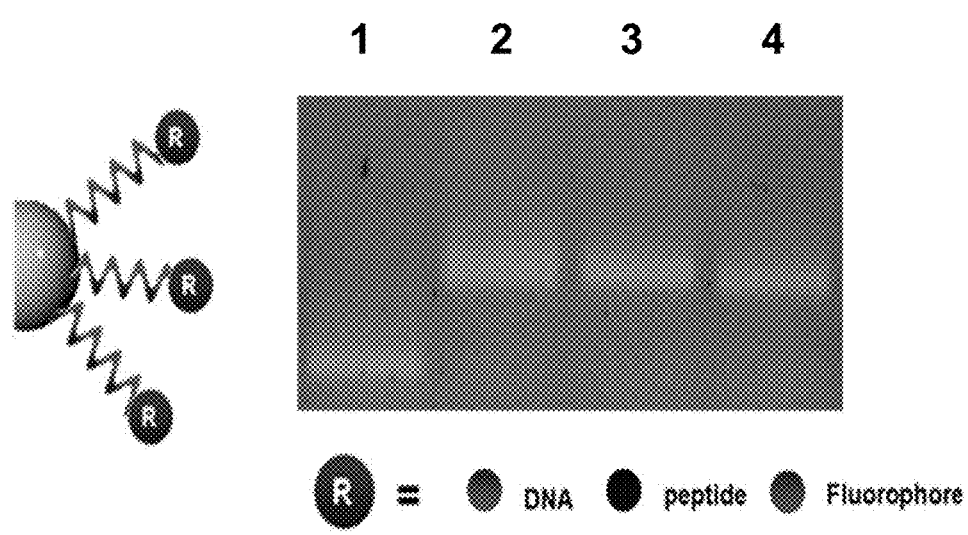
FIG. 5 shows a gel shift assay showing the change in particle size post enzymatic ligation of linker modified peptide, DNA, and dye. Lane 1 DNA-gold NPs; Lane 2 DNA-NPs post ligation to DNA strand; Lane 3 post ligation to peptide; and Lane 4 post ligation to Cy3 fluorophore using the universal linker. Ligation reaction conditions: 24 hours, 37° C., Gel conditions: 1% Agarose, 10 minutes at 200V.

To test for the ability to attach other molecules an agarose gel shift assay was utilized to see the relative degree of ligation for various different chemical groups. FIG. 5 shows the results of a gel shift assay demonstrating the change in particle size post enzymatic ligation of linker modified peptide, DNA, and dye. Lane 1 is DNA-gold NPs, lane 2 is DNA-NPs post ligation to DNA strand, lane 3 is post ligation to peptide, and lane 4 is post ligation to Cy3 fluorophore using the universal linker. The ligation reaction conditions were: 24 hours at 37° C. Gel conditions: 1% Agarose, 10 minutes at 200V.

Figure 6:
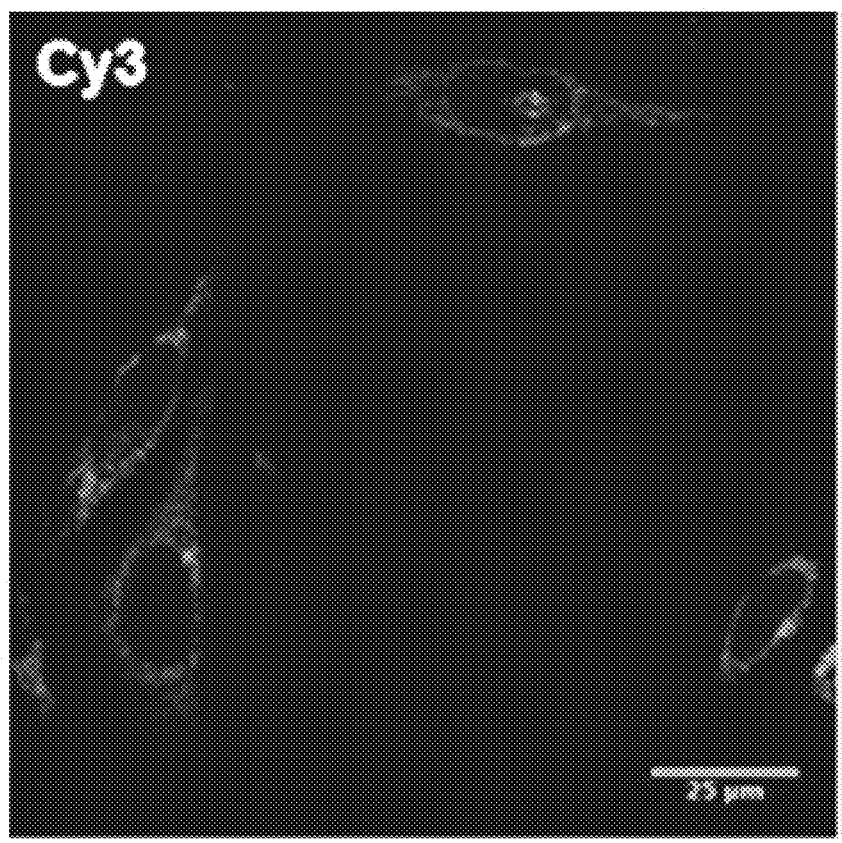
FIG. 6 shows confocal microscopy of HeLa cells incubated with dye labeled DNA-gold nanoparticles (NP) functionalized using the universal monophosphorylated linker. Cy3-alkyne linked to the universal linker was ligated to the surface of a DNA functionalized NP and incubated in HeLa cells (2 nm NPs).
Figure 7:
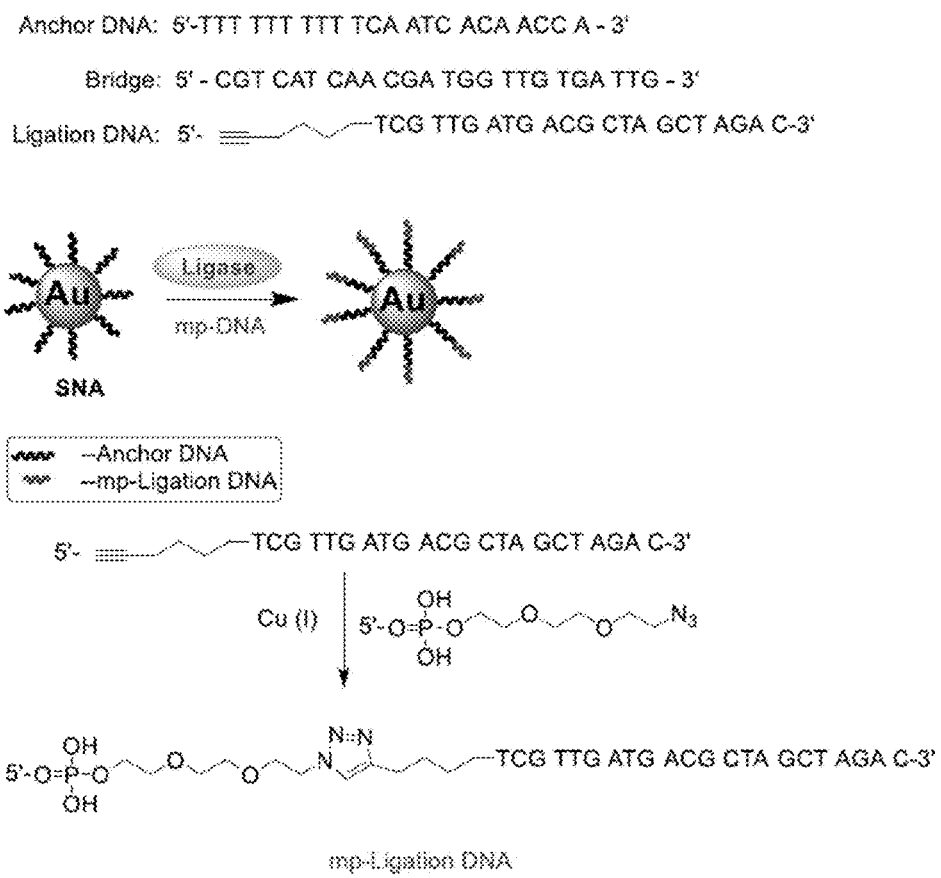
FIG. 7 shows an exemplary schematic for a universal linker enabling enzyme-mediated attachment of nucleic acids to nanoparticle surfaces (i.e., gold). Anchor DNA 5'-TTT TTT TTT TCA ATC ACA ACC A-3' (SEQ ID NO:02); Bridge 5'-CGT CAT CAA CGA TGG TTG TGA TTG-3' (SEQ ID NO:03); Ligation DNA: 5'-TCG TTG ATG ACG CTA GCT AGA C-3' (SEQ ID NO:04); mp-Ligation DNA: 5'-TCG TTG ATG ACG CTA GCT AGA C-3' (SEQ ID NO:08) where mp=monophosphorylated as the nucleic acid can be monophosphorylated via attachment of the universal linker.
Figure 8:
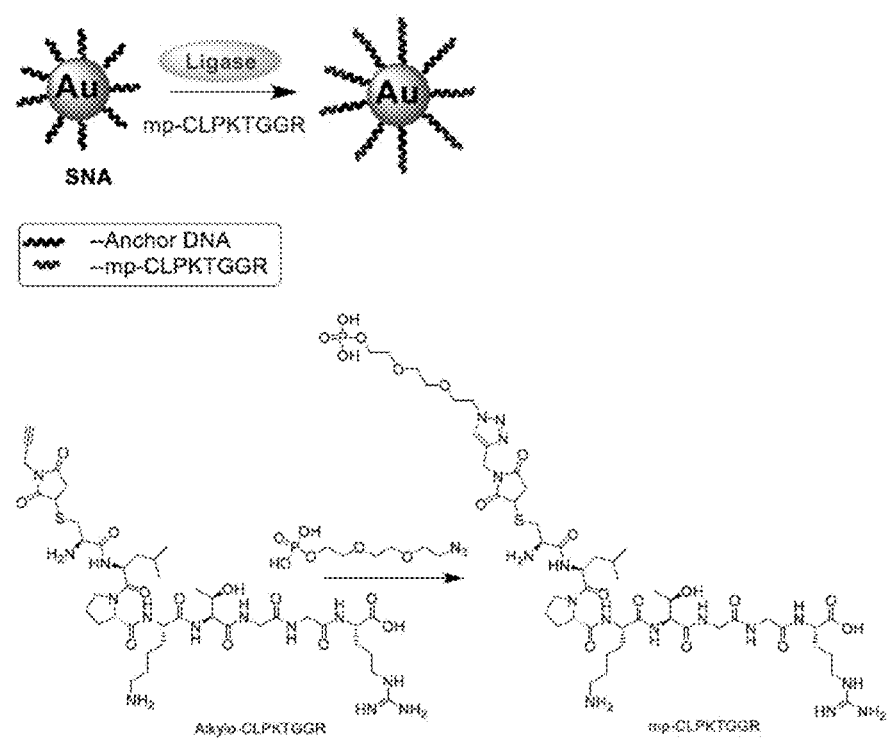
FIG. 8 shows a schematic for the use of the universal linker enabling enzyme-mediated attachment of ligands to nanoparticle surfaces (i.e., gold). Alkylo-CLPKTGGR (SEQ ID NO:05); mp-CLPKTGGR (SEQ ID NO:07) where mp=monophosphorylated as the peptide can be monophosphorylated via attachment of the universal linker.
Figure 9A:
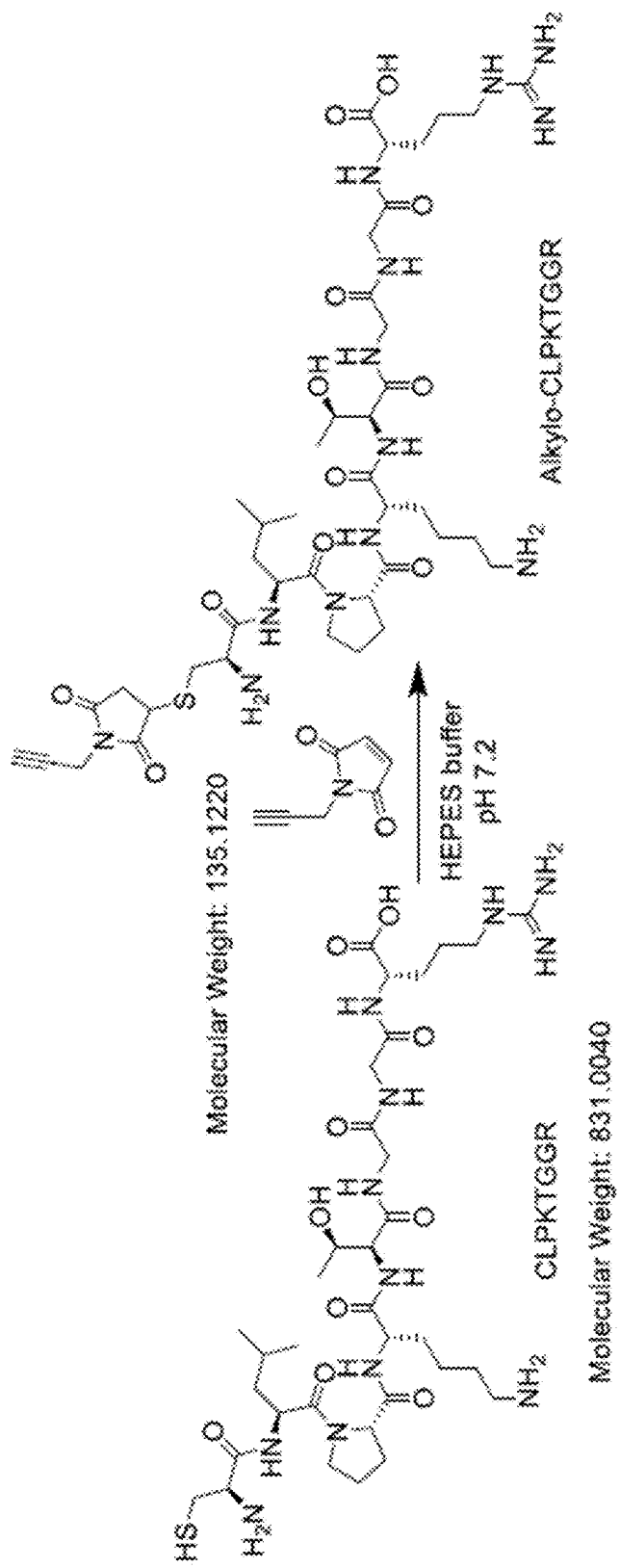
FIG. 9A shows the synthesis of alkylo-CLPKTGGR (SEQ ID NO:05) from CLPKTGGR (SEQ ID NO:01). Propargyl-maleimide (2.4 mg, 0.018 mmol) was added to a solution of sortase recognition motif (CLPKTGGR; SEQ ID NO:01) (10 mg, 0.012 mmol) in 200 µL of 5% acetonitrile in 50 mM HEPES buffer (pH=7.2), and the solution stirred at room temperature for 2 hours.
Figure 9B:
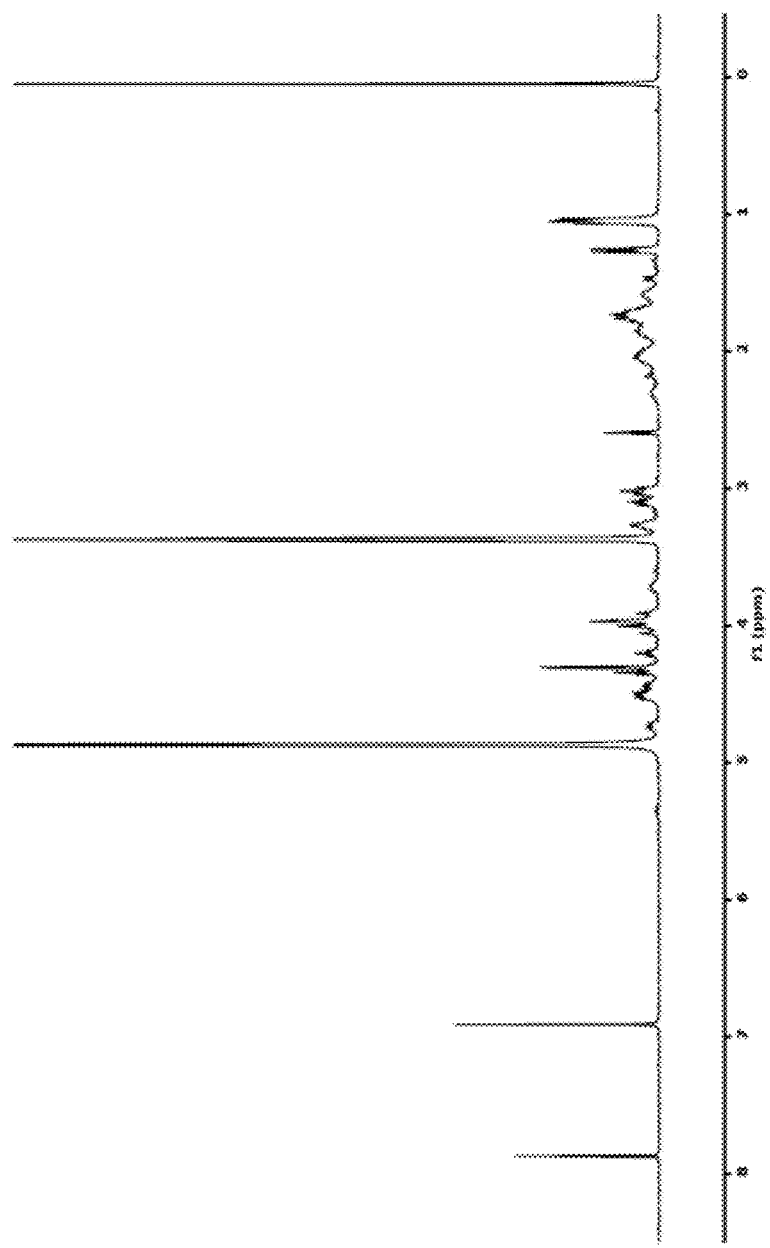
FIG. 9B shows the $^1$H NMR 300 of compound alkylo-CLPKTGGR (SEQ ID NO:05) in d-methanol/CDCl$_3$.
Figure 10A:
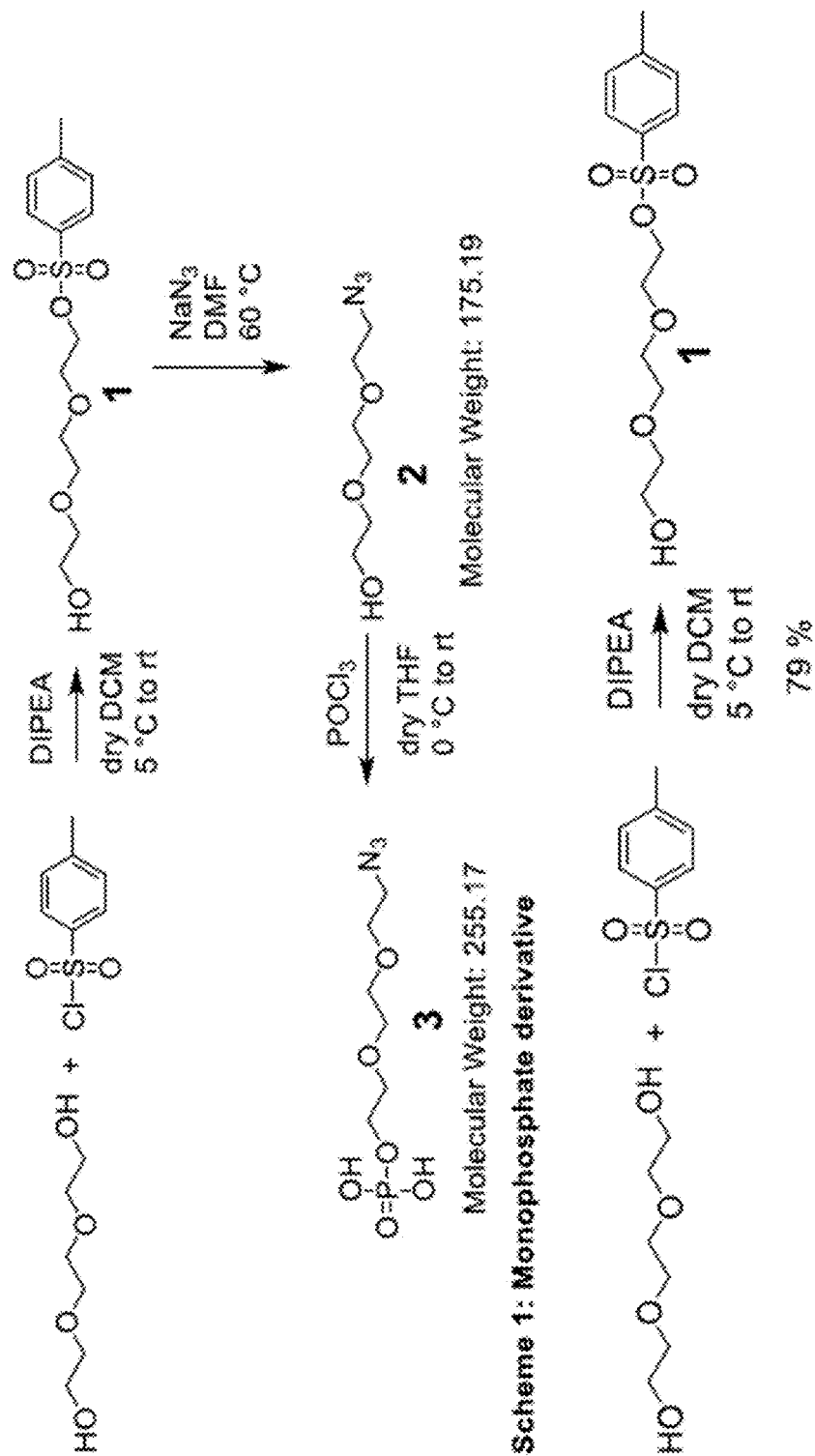
FIG. 10A shows the synthesis of compound 1. Tosyl chloride (1.00 g, 5.25 mmol) was added at 5° C. to a solution of TEG (triethylene glycol, 1.57 g, 10.5 mmol) in anhydrous methylene chloride (6 mL). This was followed by drop-wise addition of DIPEA (N,N-diisopropylethylamine, 1.0 mL, 5.77 mmol). The water bath was removed and the reaction mixture stirred at room temperature for 18 hours. The resulting mixture was diluted with water (6 mL) and washed with 1 M HCl, brine (2×10 mL), and water (3×10 mL). The solution was dried over sodium sulfate and concentrated under vacuum. The resulting residue was purified by silica gel chromatography (ethyl acetate/hexane 7:3) to obtain the product as yellow oil (1.26 g, 79%). LEN et al., "Micellar Catalysis Using a Photochromic Surfactant: Application to the Pd-Catalyzed Tsuji-Trost Reaction in Water" *J. Org. Chem.*, 79(2): 493-500 (2014).
Figure 11:
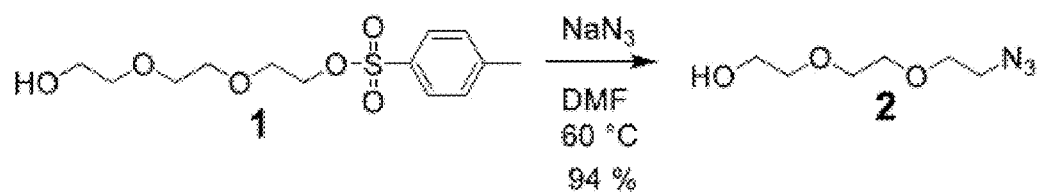
FIG. 11 shows the synthesis of compound 2 (Jka-01-003). Sodium azide (2.69 g, 41.4 mmol) was added to a solution of compound 1 (1.26 g, 4.14 mmol) in anhydrous dimethylformamide (DMF, 15 mL), and the mixture stirred at 60° C. for 16 hours. The mixture was diluted with water (20 mL) and the organic layer extracted with ethyl acetate (3×15 mL). The organic layer was washed with brine (10 mL), followed by water (2×10 mL), and dried under sodium sulfate to yield the product as brown oil.
Figure 12A:
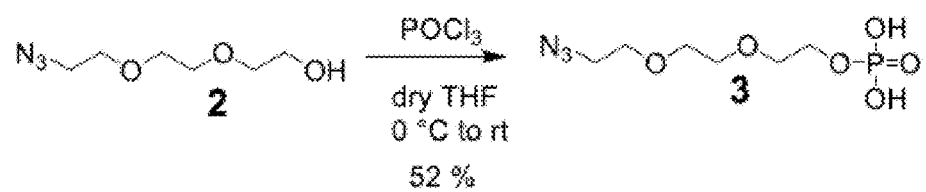
FIG. 12A shows the synthesis of compound 3. Triethylamine (0.3 mL, 2.13 mmol) was added dropwise under argon atmosphere to a 5 mL tetrahydrofuran (THF) solution of phosphoryl chloride (POCl$_3$, 180 µL, 1.94 mmol) in 50 mL round bottomed flask at 0° C. The resultant mixture was stirred for 20 minutes until a white solid precipitated. On addition of compound 2 (0.26 g, 1.48 mmol) dissolved in 1 mL anhydrous THF, the precipitate dissolved. After 2 hours, the THF was removed under reduced pressure and the sample purified by preparative TLC using methanol/methylene chloride (1:20) as eluent to afford the title compound as colorless oil. LU et al., "Carboxyl-polyethylene glycol-phosphoric acid: a ligand for highly stabilized iron oxide nanoparticles" *J. Mater. Chem.*, 22:19806-19811 (2012). GNAUCK et al., "Carboxy-Terminated Oligo(ethylene glycol)-Alkane Phosphate: Synthesis and Self-Assembly on Titanium Oxide Surfaces" Langmuir 23(2):377-381 (2007).
Figure 12B:
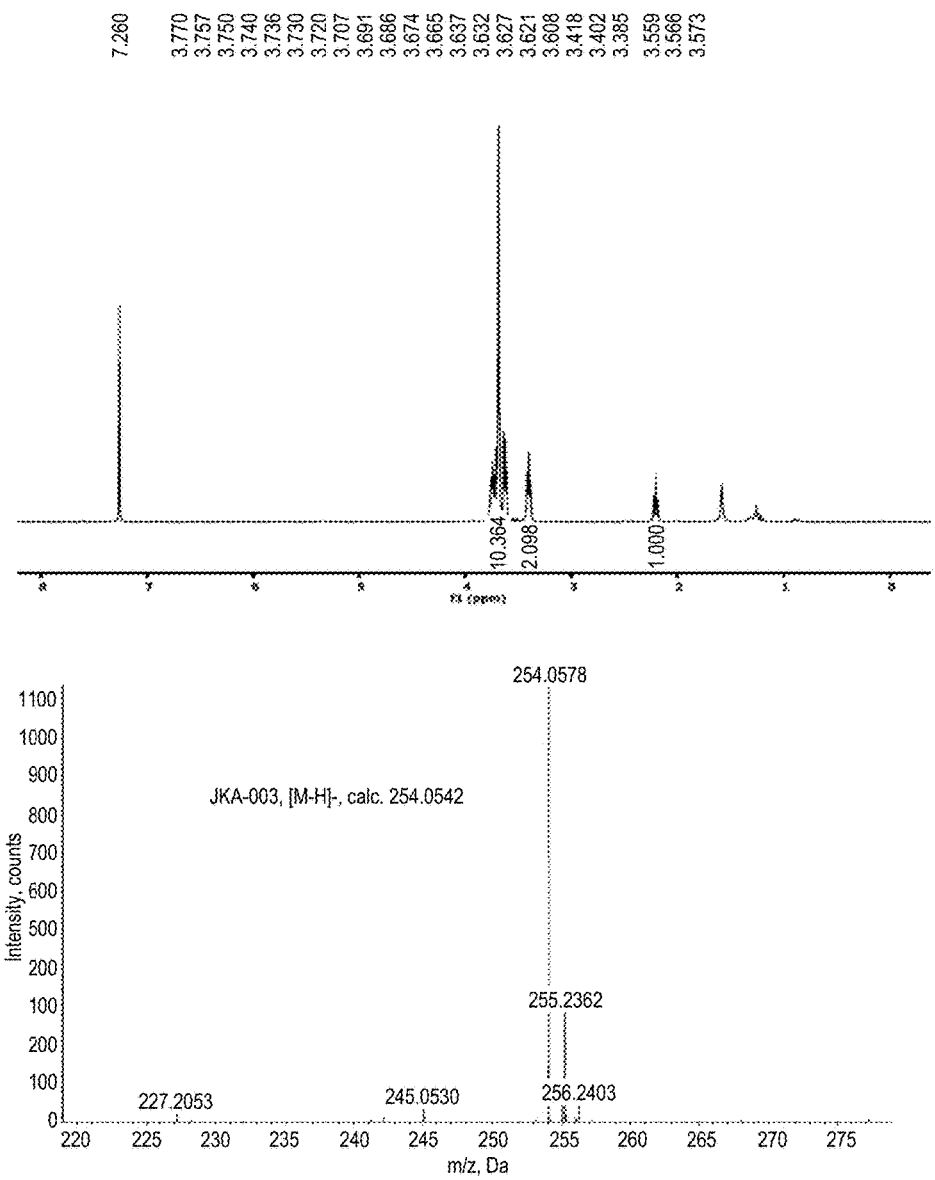
FIG. 12B shows an ESI-MS of compound 3. ESI-HRMS (m/z): [M-H]$^-$ calculation for C$_6$H$_{13}$N$_3$O$_6$P$^-$254.0547; found, 254.0578.

In addition to characterizing the change in the particles surface due to size and charge changes by dynamic light scattering (DLS) and agarose gel shift respectively, confocal microscopy was also utilized to determine the effectiveness of the linker conjugation and ability to deliver molecules into cells using this new linkage approach. To date it has been observed that DNA-functionalized nanoparticles (DNA-NPs) are able to enter cells readily in contrast to their linear nucleic acid counterparts. When immobilized and when the DNA grafting density is sufficient the DNA-NPs can engage scavenger receptors and enter cells without transfection agents. In order to test the utility of the monophosphorylated linker, an alkyne modified Cy3 dye was clicked onto the monophosphate linker and then ligated to the surface of the DNA-NP. This dye conjugated DNA was then incubated with Hela cells and evaluated for signs of fluorescence (see FIG. 6).

The results show that the linker is effective at attaching monophosphorylated material to the surface of the nanoparticle and that the nanoparticle formulation is not toxic. Such a versatile approach is important for the rapidly growing field of nucleic acid based therapeutics and offers an important strategy aimed at repurposing enzymes for use as assembly tools for functionalizing nanomaterials in a chemically specific manner.

The invention claimed is:

1. A heterobifunctional linker having the formula:

(HO)2(O)P-O-I-Y;

wherein

I is an intervening moiety, the intervening moiety having a molecular weight in the range of 100 to 10000; and Y is a chemically-reactive moiety, the chemically-reactive moiety being reactable to couple the linker to an organic compound in aqueous solution, or a salt thereof, the chemically-reactive moiety and intervening moiety being selected such that the heterobifunctional linker, or salt thereof, is water soluble at a concentration of at least 10 pM at a pH within the range of 6.5 to 7.8.

2. The heterobifunctional linker according to claim 1, wherein the chemically-reactive moiety is reactable to couple the linker to a biomolecule in aqueous solution.

3. The heterobifunctional linker according to claim 1, wherein the chemically-reactive moiety comprises an azide.

4. The heterobifunctional linker according to claim 1, wherein the chemically-reactive moiety comprises an alkyne.

5. The heterobifunctional linker according to claim 4, wherein the alkyne has the structural formula

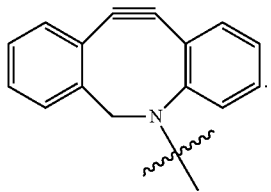

6. The heterobifunctional linker according to claim 4, wherein the alkyne has the structural formula

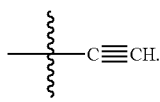

7. The heterobifunctional linker according to claim 1, wherein the chemically-reactive moiety comprises a molecule selected from the group consisting of an alkene, an amine, a maleimide, a carboxylate, a carboxylate ester of N-hydroxysuccinimide, a (3-carboxy-4-nitrophenyl)disulfanyl, a cyclopentadiene, an iodoacetamide, an isocyanate, isothiocyanate, a (pyridin-2-yl)disulfanyl, and a thiol.

8. The heterobifunctional linker according to claim 7, wherein the chemically-reactive moiety comprises an alkene and the alkene is a terminal alkene.

9. The heterobifunctional linker according to claim 1, wherein the chemically-reactive moiety is reactive in a cycloaddition at a temperature below 60° C.

10. The heterobifunctional linker according to claim 1, wherein the intervening moiety comprises an entity selected from the group consisting of a polyethylene glycol, a polyethyleneimine, a copolymer or cooligomer of ethylene glycol and ethyleneimine, a peptide oligomer or polypeptide, a polyester of one or more of lactic acid and glycolic acid, a poly(propylene glycol), and a poly(ethylene glycol-co-propylene glycol).

11. The heterobifunctional linker according to claim 10, wherein the intervening moiety comprises a polyethyelene glycol having structure —$(CH_2CH_2O)_n$— in which n is in the range of 3-200.

12. The heterobifunctional linker according to claim 11, wherein the intervening moiety comprises the structure —$(CH_2CH_2O)_n$—$(CH_2)_m$— in which m is in the range of 1-6.

13. The heterobifunctional linker according to claim 10, wherein the intervening moiety comprises a polyester of one or more of lactic acid and glycolic acid, and wherein the polyester comprises poly(lactic acid-co-glycolic acid).

14. The heterobifunctional linker according to claim 1, wherein the intervening moiety comprises the structure -(L)-$(CH_2)_m$— in which m is in the range of 1-6, and in which L comprises a polyethylene glycol, a polyethyleneimine, a copolymer or cooligomer of polyethylene glycol and polyethyleneimine, a peptide oligomer or polypeptide, a polyester of one or more of lactic acid and glycolic acid, a poly(propylene glycol), or a poly(ethylene glycol-co-propylene glycol).

15. The heterobifunctional linker according to claim 1, wherein there are no branched carbon atoms or nitrogen atoms within 4 atoms of a branched carbon atom or nitrogen atom being defined as having more than three non-hydrogen, non-carbonyl substituents directly bound thereto.

16. The heterobifunctional linker according to claim 1, wherein the heterobifunctional linker has a molecular weight in the range of 100-10000.

17. The heterobifunctional linker according to claim 1, having the structure:

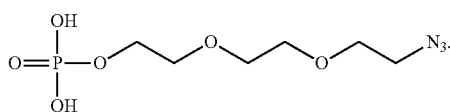 [SMILES: [N-]=[N+]=NCCOCCOCCOP(=O)(O)O]

18. A composition comprising the heterobifunctional linker of claim 1, wherein the phosphate moiety of the heterobifunctional linker is covalently bound to a first molecule.

19. The composition according to claim 18, wherein the first molecule is a nucleic acid, and wherein the phosphate moiety of the heterobifunctional linker is covalently bound to a 3'-hydroxyl of a phosphate moiety of the nucleic acid to form a phosphodiester.

20. The composition according to claim 19, wherein the nucleic acid is a DNA of a DNA-coated nanoparticle.

21. The composition according to claim 18, wherein the reactive moiety of the heterobifunctional linker is covalently bound to a second molecule.

22. A composition comprising the heterobifunctional linker of claim 1, wherein the chemically-reactive moiety of the heterobifunctional linker is covalently bound to a second molecule.

23. The composition according to claim 21, wherein the second molecule is selected from the group consisting of a polypeptide, a nucleic acid, a dye, a lipid, a sterol, a fatty acid, and a polymer.

24. The composition according to claim 21, wherein:
(a) the chemically-reactive moiety of the heterobifunctional linker comprises an azide, and the heterobifunctional linker is covalently bound to the second molecule through a thiazole formed from the azide and an alkyne;
(b) the chemically-reactive moiety of the heterobifunctional linker comprises an alkyne, and the heterobifunctional linker is covalently bound to the second molecule through a thiazole formed from the alkyne and an azide;
(c) the chemically-reactive moiety of the heterobifunctional linker comprises a cyclopentadiene, and the heterobifunctional linker is covalently bound to the second molecule through a cycloaddition product of the cyclopentadiene;
(d) the chemically-reactive moiety of the heterobifunctional linker comprises a thiol, and the heterobifunctional linker is covalently bound to the second molecule through a thiol-ene or thiol-yne reaction product of the thiol;
(e) the chemically-reactive moiety of the heterobifunctional linker comprises an alkene, and the heterobifunctional linker is covalently bound to the second molecule through a thiol-ene reaction product of the alkene;
(f) the chemically-reactive moiety of the heterobifunctional linker comprises a maleimide, and the heterobifunctional linker is covalently bound to the second molecule through a thiol-ene reaction product of the maleimide;
(g) the chemically-reactive moiety of the heterobifunctional linker comprises an alkyne, and the heterobifunctional linker is covalently bound to the second molecule through a thiol-ene reaction product of the alkyne;
(h) the chemically-reactive moiety of the heterobifunctional linker comprises a carboxylate and the heterobifunctional linker is covalently bound to the second molecule through a condensation reaction product of the carboxylate;
(i) the chemically-reactive moiety of the heterobifunctional linker comprises an amine and the heterobifunctional linker is covalently bound to the second molecule through a condensation reaction product of the amine;
(j) the chemically-reactive moiety of the heterobifunctional linker comprises a carboxylate ester of N-hydroxysuccinimide and the heterobifunctional linker is covalently bound to the second molecule through a condensation reaction product of the a carboxylate ester of N-hydroxysuccinimi de;
(k) the chemically-reactive moiety of the heterobifunctional linker comprises an isocyanate or an isothiocyanate and the heterobifunctional linker is covalently bound to the second molecule through a reaction product of the isocyanate or isothiocyanate;
(l) the chemically-reactive moiety of the heterobifunctional linker comprises an iodoacetamide and the heterobifunctional linker is covalently bound to the second molecule through a reaction product of the iodoacetamide; or
(m) the chemically-reactive moiety of the heterobifunctional linker comprises a (pyridin-2-yl)disulfanyl or a (3-carboxy-4-nitrophenyl)disulfanyl and the heterobifunctional linker is covalently bound to the second molecule through a reaction product of the (pyridin-2-yl)disulfanyl or (3-carboxy-4-nitrophenyl)disulfanyl iodoacetamide.

25. The composition according to claim 21, wherein the reactive moiety of the heterobifunctional linker is reactive in a cycloaddition at a temperature below 60° C., and the heterobifunctional linker is covalently bound to the second molecule through a cycloaddition reaction product of the chemically-reactive moiety.

* * * * *